United States Patent
Yagyu et al.

(10) Patent No.: US 10,646,487 B2
(45) Date of Patent: May 12, 2020

(54) MELANIN PRODUCTION INHIBITOR, WHITENING AGENT, FIBROBLAST ACTIVATOR, COLLAGEN AND/OR ELASTIN PRODUCTION PROMOTOR AND WRINKLE AMELIORANT

(71) Applicant: SHOWA DENKO K.K., Tokyo (JP)

(72) Inventors: Daisuke Yagyu, Chiba (JP); Yuko Nakagami, Fujisawa (JP); Ryota Niibayashi, Honjo (JP); Eiko Kato, Tokyo (JP)

(73) Assignee: SHOWA DENKO K.K., Tokyo (JP)

( * ) Notice: Subject to any disclaimer, the term of this patent is extended or adjusted under 35 U.S.C. 154(b) by 0 days.

(21) Appl. No.: 16/314,960

(22) PCT Filed: Jun. 8, 2017

(86) PCT No.: PCT/JP2017/021336
§ 371 (c)(1),
(2) Date: Jan. 3, 2019

(87) PCT Pub. No.: WO2018/012157
PCT Pub. Date: Jan. 18, 2018

(65) Prior Publication Data
US 2019/0224199 A1  Jul. 25, 2019

(30) Foreign Application Priority Data
Jul. 14, 2016  (JP) .................. 2016-139465

(51) Int. Cl.
| | | |
|---|---|---|
| *A61K 31/513* | (2006.01) | |
| *A61Q 19/02* | (2006.01) | |
| *A61Q 19/08* | (2006.01) | |
| *A61P 17/16* | (2006.01) | |
| *A61K 8/49* | (2006.01) | |

(52) U.S. Cl.
CPC .............. *A61K 31/513* (2013.01); *A61K 8/49* (2013.01); *A61K 8/4953* (2013.01); *A61P 17/16* (2018.01); *A61Q 19/02* (2013.01); *A61Q 19/08* (2013.01)

(58) Field of Classification Search
CPC ...... A61K 31/513; A61K 8/49; A61K 8/4953; A61P 17/16; A61Q 19/02; A61Q 19/08
USPC ........................................................... 544/224
See application file for complete search history.

(56) References Cited

FOREIGN PATENT DOCUMENTS

| JP | 43-014708 B1 | 6/1968 |
|---|---|---|
| JP | 47-019559 B1 | 6/1972 |
| JP | 62-019511 A | 1/1987 |
| JP | 2011-098896 A | 5/2011 |
| JP | 5066448 B2 | 11/2012 |
| JP | 5788715 B2 | 10/2015 |
| WO | 2009/076743 A1 | 6/2009 |
| WO | 2010/005123 A1 | 1/2010 |

OTHER PUBLICATIONS

National Center for Biotechnology Information. PubChem Database. AKOS009161944, Source=AKos Consulting & Solutions, SID=145473207, https://pubchem.ncbi.nlm.nih.gov/substance/145473207 (accessed on Aug. 6, 2019). Available to the public on Oct. 18, 2012. (Year: 2012).*
National Center for Biotechnology Information. PubChem Database. SID 285441860, Source=Aurora Fine Chemicals LLC, SID= 285441860, https://pubchem.ncbi.nlm.nih.gov/substance/285441860 (accessed on Aug. 6, 2019). Available to the public on Jan. 15, 2016. (Year: 2016).*
National Center for Biotechnology Information. PubChem Database. SID 293636194, Source=Aurora Fine Chemicals LLC, SID= 293636194, https://pubchem.ncbi.nlm.nih.gov/substance/293636194 (accessed on Aug. 6, 2019). Available to the public on Jan. 20, 2016. (Year: 2016).*
STN Registry Database, Record for RN 13156-42-8, entered into database on Nov. 16, 1984. (Year: 1984).*
STN Registry Database, Record for RN 1105534-20-0, entered into database on Feb. 13, 2009. (Year: 2009).*

(Continued)

*Primary Examiner* — Daniel R Carcanague
(74) *Attorney, Agent, or Firm* — Sughrue Mion, PLLC

(57) ABSTRACT

The present invention provides an agent containing an orotic acid derivative that has high solubility in solvent and has superior physiological activity. The agent of the present invention is a melanin production inhibitor, whitening agent, fibroblast activator, collagen and/or elastin production promoter or wrinkle ameliorant containing as an active ingredient thereof an orotic acid derivative represented by the following general formula (1) or a salt thereof. In formula (1), R preferably represents a side chain of glutamic acid, glycine, histidine or aspartic acid. [In formula (1), R represents a side chain of a naturally-occurring amino acid and R may form, together with a nitrogen atom adjacent thereto through a single carbon atom, a hetero ring].

[Chemical Formula 1]

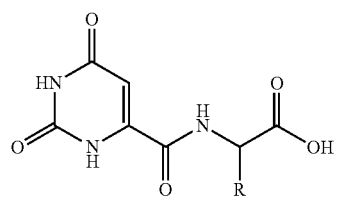

(1)

15 Claims, 1 Drawing Sheet

(56) References Cited

OTHER PUBLICATIONS

STN Registry Database, Record for RN 1924745-17-4, entered into database on Jun. 5, 2016. (Year: 2016).*
STN Registry Database, Record for RN 1104798-59-5, entered into database on Feb. 12, 2009. (Year: 2009).*
Chemical Abstracts, CAPLUS Database, Abstract for Japanese Patent JP 43014708, published on Jun. 21, 1968. (Year: 1968).*
T.S. Safonova et al., "Researches on Heterocyclic Rings Containing Nitrogen and Sulfur", Chemistry of Heterocyclic Compounds, Jul. 1967, pp. 287-290, vol. 3, Issue 4.
International Search Report of PCT/JP2017/021336 dated Aug. 8, 2017 [PCT/ISA/210].
Crosby D G et al: "Orotylamino Acids.", Journal of Medicinal Chemistry May 1963, vol. 6, May 1963 (May 1963), pp. 334-335, ISSN: 0022-2623.
Extended European Search Report dated Mar. 23, 2020, for Application No. 17827289.4; 7 pages.

* cited by examiner

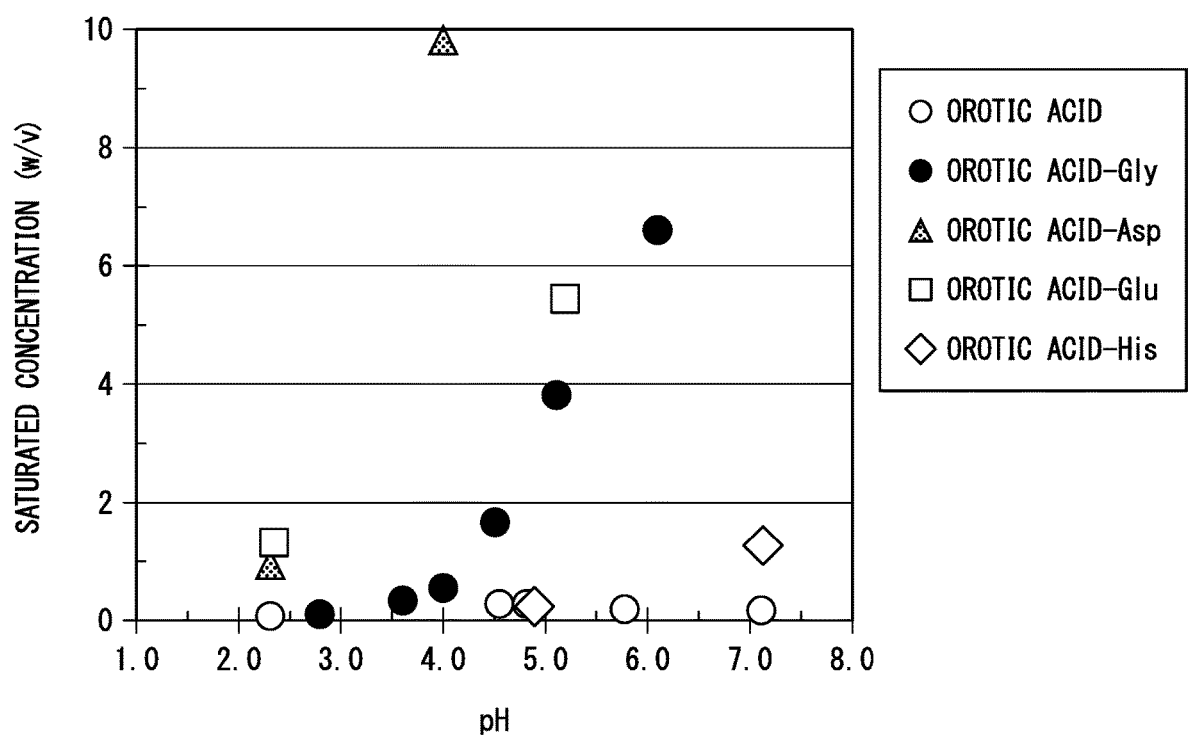

MELANIN PRODUCTION INHIBITOR, WHITENING AGENT, FIBROBLAST ACTIVATOR, COLLAGEN AND/OR ELASTIN PRODUCTION PROMOTOR AND WRINKLE AMELIORANT

CROSS REFERENCE TO RELATED APPLICATIONS

This application is a National Stage of International Application No. PCT/JP2017/021336, filed Jun. 8, 2017, claiming priority based on Japanese Patent Application No. 2016-139465, filed Jul. 14, 2016.

TECHNICAL FIELD

The present invention relates to: a melanin production inhibitor, a whitening agent, a fibroblast activator, a collagen and/or elastin production promoter, and a wrinkle ameliorant, having as an active ingredient thereof a specific orotic acid derivative or salt thereof.

BACKGROUND ART

Orotic acid is an heteroaromatic ring compound produced from carbamoyl phosphate and aspartic acid that functions as an intermediate during biosynthesis of pyrimidine bases of nucleic acids in the body. Although it was discovered as a growth promoting factor in mice and is also known as vitamin B13, it is not an essential amino acid since it can be biosynthesized by numerous higher animals including humans.

Orotic acid is known to have various actions effective for maintaining and promoting health, such as a uric acid level lowering action (Patent Document 1), anti-inflammatory action, nutritional enhancement action or liver function promoting action. In addition, stomatitis preventive and therapeutic agents (Patent Document 2) and energy consumption-reducing agents for improving endurance (Patent Document 3) containing orotic acid have been reported. In addition, promotion of the production of hyaluronic acid and glucosaminoglycans has been reported regarding its usefulness for skin (Patent Document 4).

The production of orotic acid derivatives has also been examined. Patent Document 5 proposes an acid amide-type orotic acid derivative and a production method thereof. However, there are no disclosures regarding the physiological activity of these compounds.

PRIOR ART DOCUMENTS

Patent Documents

[Patent Document 1] Japanese Unexamined Patent Application, First Publication No. 2011-98896
[Patent Document 2] Japanese Patent No. 5066448
[Patent Document 3] Japanese Patent No. 5788715
[Patent Document 4] International Publication No. WO 2010/005123
[Patent Document 5] International Publication No. WO 2009/076743
[Patent Document 6] Japanese Examined Patent Application, Second Publication No. S43-14708

Non-Patent Documents

Chemistry of Heterocyclic Compounds, July 1967, Vol. 3, Issue 4, pp. 287-290, "Researches on Heterocyclic Rings Containing Nitrogen and Sulfur"

DISCLOSURE OF THE INVENTION

Problems to be Solved by the Invention

Since orotic acid is extremely insoluble in water and practically insoluble in alcohol such as ethanol, it was not necessary used satisfactorily when incorporating in products such as external skin preparations, cosmetics or food additives.

Therefore, an object of the present invention is to provide an agent containing an orotic acid derivative that overcomes these difficulties by having high solubility in solvent and superior physiological activity.

Means for Solving the Problems

The inventors of the present invention found that an orotic acid derivative represented by the following general formula (1) has improved solubility in solvent and has superior action such as melanin production inhibitory action, fibroblast activating action, or collagen and/or elastin production promoting action, thereby leading to completion of the present invention.

Namely, the present invention provides the means indicated below.

[1] A melanin production inhibitor comprising as an active ingredient thereof an orotic acid derivative represented by the following general formula (1) or a salt thereof:

[Chemical Formula 1]

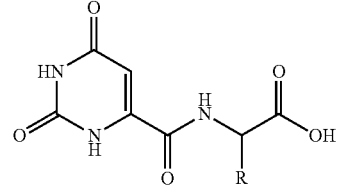

(1)

(wherein, R represents a side chain of a naturally-occurring amino acid and R may form, together with a nitrogen atom adjacent thereto through a single carbon atom, a hetero ring).

[2] A whitening agent comprising as an active ingredient thereof an orotic acid derivative represented by the following general formula (1) or a salt thereof:

[Chemical Formula 2]

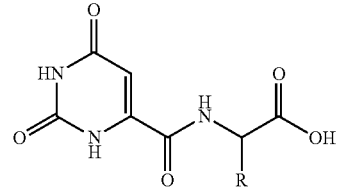

(1)

(wherein, R represents a side chain of a naturally-occurring amino acid and R may form, together with a nitrogen atom adjacent thereto through a single carbon atom, a hetero ring).

[3] A fibroblast activator comprising as an active ingredient thereof an orotic acid derivative represented by the following general formula (1) or a salt thereof:

[Chemical Formula 3]

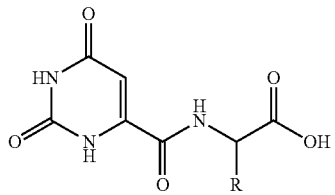
(1)

(wherein, R represents a side chain of a naturally-occurring amino acid and R may form, together with a nitrogen atom adjacent thereto through a single carbon atom, a hetero ring).

[4] A collagen and/or elastin production promoter comprising as an active ingredient thereof an orotic acid derivative represented by the following general formula (1) or a salt thereof:

[Chemical Formula 4]

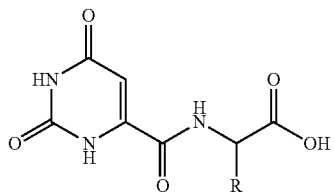
(1)

(wherein, R represents a side chain of a naturally-occurring amino acid and R may form, together with a nitrogen atom adjacent thereto through a single carbon atom, a hetero ring).

[5] A wrinkle ameliorant comprising as an active ingredient thereof an orotic acid derivative represented by the following general formula (1) or a salt thereof:

[Chemical Formula 5]

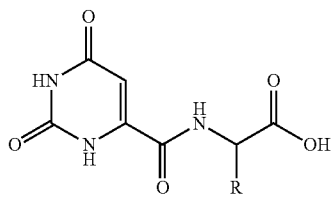
(1)

(wherein, R represents a side chain of a naturally-occurring amino acid and R may form, together with a nitrogen atom adjacent thereto through a single carbon atom, a hetero ring).

[6] The agent described in any of [1] to [5] above, which is an external skin preparation.

[7] The agent described in any of [1] to [6] above, which is a cosmetic.

[8] The agent described in any of [1] to [7] above, wherein the concentration of the orotic acid derivative or salt thereof is $1.0 \times 10^{-6}$% (w/v) to 10% (w/v).

[9] The agent described in any of [1] to [8] above, wherein the orotic acid derivative has a higher solubility in water than orotic acid.

[10] The agent described in any of [1] to [9] above, wherein R in the formula (1) represents a side chain of a hydrophilic amino acid.

[11] The agent described in any of [1] to [9] above, wherein R in the formula (1) represents a side chain of glutamic acid, glycine, histidine or aspartic acid.

[12] The agent described in any of [1] to [11] above, which contains water and the water content is 1% by weight to 99.9% by weight.

[13] The agent described in [12] above, wherein the pH is 2 to 8.

Effects of the Invention

The agents according to the present invention are such that the orotic acid derivative contained therein has high solubility in solvent and has superior action such as melanin production inhibitory action, fibroblast activating action or collagen and/or elastic production promoting action. The agents according to the present invention can also be provided as a whitening agent, wrinkle ameliorant

BRIEF DESCRIPTION OF THE DRAWINGS

FIG. 1 is a graph indicating the results of comparing the saturated concentrations of orotic acid and various orotic acid derivatives in examples when respectively dissolved in water.

EMBODIMENTS FOR CARRYING OUT THE INVENTION

<Orotic Acid Derivatives>

The following provides an explanation of orotic acid derivatives according to the present invention.

The orotic acid derivatives according to the embodiments are compounds represented by the following general formula (1). The orotic acid derivatives according to the present invention are compounds in which orotic acid and an amino group of a naturally-occurring amino acid have undergone dehydration condensation to form an amide bond.

[Chemical Formula 6]

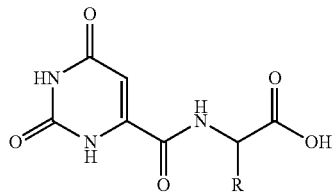
(1)

[In formula (1), R represents a side chain of a naturally-occurring amino acid and R may form, together with a nitrogen atom adjacent thereto through a single carbon atom, a hetero ring.]

In general formula (1), R represents a side chain of a naturally-occurring amino acid. However, in the case the naturally-occurring amino acid is proline, R may form, together with a nitrogen atom adjacent thereto through a single carbon atom, a hetero ring. Namely, in the case the naturally-occurring amino acid is proline, general formula (1) indicates the following formula (1-5). In the present description, a "naturally-occurring amino acid" refers to any of the 20 types of amino acids that compose proteins.

Examples of the aforementioned 20 types of amino acids include alanine, cysteine, aspartic acid, glutamic acid, phenylalanine, glycine, histidine, isoleucine, lysine, leucine, methionine, asparagine, proline, glutamine, arginine, serine, threonine, valine, tryptophan and tyrosine. Furthermore, in the case the naturally-occurring amino acid is proline, R in formula (1) may form, together with a nitrogen atom adjacent thereto through a single carbon atom, a hetero ring.

The aforementioned 20 types of naturally-occurring amino acids can be represented with the following general formula (2):

[Chemical Formula 7]

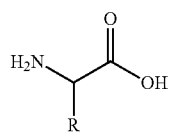

(2)

(wherein, R has the same meaning as in the aforementioned formula (1) and R may form, together with a nitrogen atom adjacent thereto through a single carbon atom, a hetero ring).

R representing a side chain represents "—$C_2H_4COOH$" when the naturally-occurring amino acid is glutamic acid, "—H" when the naturally-occurring amino acid is glycine, and "—$CH_3$" when the naturally-occurring amino acid is alanine. This applies similarly to other naturally-occurring amino acids.

The orotic acid derivatives of the embodiments have a structural moiety derived from a naturally-occurring amino acid. Consequently, even if a orotic acid derivative is subjected to decomposition, the amino acid moiety formed as a result of that decomposition is the same as amino acids present in the body and is highly safe.

Naturally-occurring amino acids can be classified into hydrophilic amino acids and hydrophobic amino acids according to the type of side chain. In the present description, hydrophilic naturally-occurring amino acids refer to glycine, serine, threonine, cysteine, tyrosine, asparagine, glutamine, aspartic acid, glutamic acid, lysine, arginine and histidine. Among these, the hydrophilic naturally-occurring amino acid is preferably glutamic acid, glycine, histidine or aspartic acid. In the present description, hydrophobic naturally-occurring amino acids refers to alanine, valine, leucine, isoleucine, methionine, phenylalanine, tryptophan and proline.

The orotic acid derivatives of the embodiments preferably have higher solubility in water than orotic acid. By improving solubility in water, the number of types of drug formulations that can be applied increases. In addition, the various types of effects subsequently described improve in comparison with orotic acid. The solubility in water of orotic acid and orotic acid derivatives can be determined by the method described in the examples.

The naturally-occurring amino acid in formula (1) is preferably a hydrophilic amino acid. An orotic acid derivative in which R represents a side chain of a hydrophilic amino acid has improved solubility in water in comparison with orotic acid, thereby making it preferable.

In addition, compounds represented by general formula (1) can have a plurality of stereoisomers such as having an asymmetric carbon in a molecule thereof. In the present description, although compounds represented by general formula (1) are described as only one form of isomer or are described without distinguishing between isomers, Compound (1) contained in the agents of the embodiments also includes other stereoisomers and all of these stereoisomers are included in the compound represented by general formula (1) and a salt thereof of the present embodiment.

The aforementioned naturally-occurring amino acid may be an L-amino acid. In the case the aforementioned naturally-occurring amino acid is an L-amino acid, compounds represented by the aforementioned formula (1) can be represented with the following general formula (1L).

[Chemical Formula 8]

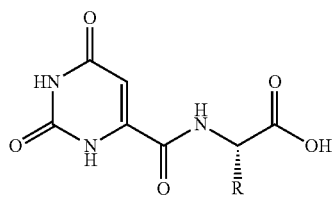

(1L)

One example of an orotic acid derivative according to the present invention is a compound represented by the following formula (1-1). This derivative is a derivative of glutamic acid.

[Chemical Formula 9]

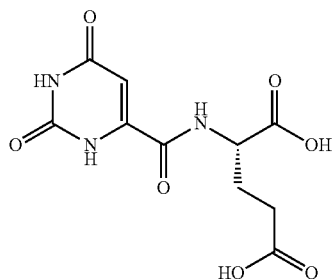

(1-1)

One example of an orotic acid derivative according to the present invention is a compound represented by the following formula (1-2). This derivative is a derivative of glycine.

[Chemical Formula 10]

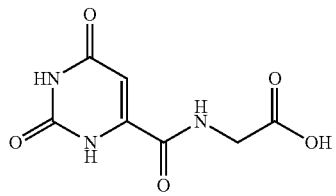

(1-2)

One example of an orotic acid derivative according to the present invention is a compound represented by the following formula (1-3). This derivative is a derivative of histidine.

[Chemical Formula 11]

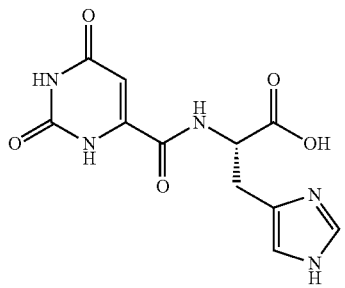

(1-3)

One example of an orotic acid derivative according to the present invention is a derivative represented by the following formula (1-4). This derivative is a derivative of aspartic acid.

[Chemical Formula 12]

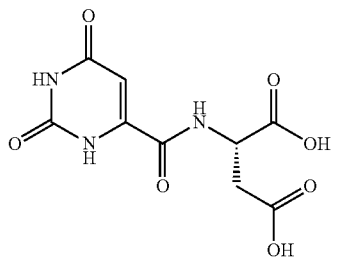

(1-4)

One example of an orotic acid derivative according to the present invention is a derivative represented by the following formula (1-5). This derivative is a derivative of proline.

[Chemical Formula 13]

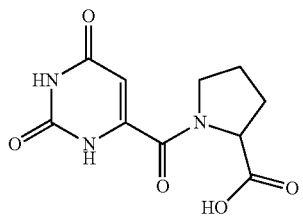

(1-5)

<Salts of Orotic Acid Derivatives>

Salts of orotic acid derivatives of the embodiments are salts of compounds represented by the aforementioned general formula (1) (to be abbreviated as Compound (1)), and are compounds formed by an anion (or cation) derived from Compound (1) and cation (or anion) derived from a compound other than Compound (1).

Examples of salts of Compound (1) include salts formed by the reaction of Compound (1) with an acid or base. Such salts may be salts formed between Compound (1) functioning as a cation and an anion or salts formed between Compound (1) functioning as an anion and a cation.

In addition, the cation and anion that compose a salt of a single molecule of Compound (1) may be only one cation and anion or two or more cations and anions. In the case of two or more cations and anions, these cations or anions may all be the same, may all be different or only a portion thereof may be the same.

Salts of Compound (1) are preferably electrically neutral in terms of the entire molecule, or in other words, the total value of the valence of cations and the total value of the valence of anions contained in a salt of a single molecule of Compound (1) are preferably the same.

The anion that forms a salt of Compound (1) together with Compound (1) functioning as a cation may be an inorganic anion or an organic anion. In addition, there are no particular limitations on the valences of the inorganic anion and organic anion and may have a valence of 1 or a valence of 2 or more.

Preferable examples of inorganic anions include nitrate ions, sulfate ions, carbonate ions, bicarbonate ions and halogen ions. Examples of the aforementioned halogen ions include fluoride ions, chloride ions, bromide ions and iodide ions.

Preferable examples of organic anions include anions of carboxylic acids.

The aforementioned anions of carboxylic acids may be anions of monocarboxylic acids (monovalent carboxylic acids) or anions of polyvalent carboxylic acids such as dicarboxylic acids or tricarboxylic acids.

Examples of the aforementioned anions of carboxylic acids include anions of saturated or unsaturated fatty acids such as formate ions, acetate ions, propanoate (propionate) ions, butanoate (butyrate) ions, pentanoate (valerate) ions, hexanoate (caproate) ions, heptanoate (enanthate) ions, octanoate (caprylate) ions, nonanoate (pelargonate) ions, decanoate (caprate) ions, dodecanoate (laurate) ions, tetradecanoate (myristate) ions, pentadecanoate ions, hexadecanoate (palmitate) ions, heptadecanoate ions, octadecanoate (stearate) ions, eicosanoate (arachidate) ions, cis-9-octadecenoate (oleate) ions, cis,cis-9,12-octadecadienoate (linoleate) ions, cis,cis,cis-9,12,15-octadecatrienoate (α-linolenate) ions, all-cis-6,9,12-octadecatrienoate (γ-linolenate) ions, and (5Z,8Z,11Z,14Z)-eicosa-5,8,11,14-tetraenoate (arachidonate) ions, anions of saturated or unsaturated dicarboxylic acids such as oxalate ions, malonate ions, succinate ions, glutarate ions, adipate ions, fumarate ions or maleate ions, and anions of hydroxy acids such as citrate ions, tartrate ions or hydroxycitrate ions.

Furthermore, in the present description, a "fatty acid" refers to a monocarboxylic acid having a linear structure unless specifically indicated otherwise.

The number of carbon atoms of the aforementioned anions of saturated or unsaturated fatty acids is preferably 2 to 25 and more preferably 3 to 20. In addition, anions of unsaturated fatty acids preferably have 1 to 4 unsaturated bonds.

The number of carbon atoms of the aforementioned anions of saturated or unsaturated dicarboxylic acids is preferably 2 to 6 and more preferably 2 to 4. In addition, anions of unsaturated dicarboxylic acids having 2 or more carbon atoms preferably have one unsaturated bond.

Among those anions that form a salt of the aforementioned Compound (1) together with Compound (1) functioning as a cation, one or more types of anions selected from the group consisting of nitrate ions, sulfate ions, carbonate ions, bicarbonate ions, halogen ions, formate ions, acetate ions, citrate ions, tartrate ions, oxalate ions and fumarate ions are particularly preferable.

The cation that forms a salt of Compound (1) together with Compound (1) functioning as an anion may be an inorganic cation or organic cation. In addition, there are no particular limitations on the valence of the inorganic cation and the organic cation, and may be one or two or more.

Preferable examples of inorganic cations include sodium ions, potassium ions, calcium ions, magnesium ions, lithium ions, barium ions, aluminum ions, zinc ions, copper ions ($Cu^+$, $Cu^{2+}$), iron ions ($Fe^{2+}$, $Fe^{3+}$), manganese ions, nickel ions, tin ions ($Sn^{2+}$, $Sn^{4+}$) and ammonium ions.

Among the aforementioned cations that form a salt of Compound (1) together with Compound (1) functioning as an anion, one or more types of cations selected from the group consisting of sodium ions, potassium ions, calcium ions, magnesium ions, zinc ions and ammonium ions are particularly preferable.

The Compound (1) and salt of Compound (1) that may be contained in the agents of the embodiments may be present alone or may be present in the state of a mixture of Compound (1) and a salt of Compound (1).

(A Method of Synthesizing Orotic Acid Derivatives)

There are no particular limitations on the method used to synthesize orotic acid derivatives and these derivatives can be suitably synthesized by a conventionally known peptide synthesis method. Specific examples thereof include a method consisting of directly condensing orotic acid with an amino acid through forming orotic acid chloride, a method consisting of condensing orotic acid and an amino acid ester using various types of coupling reagents such as dicyclohexyl carbodiimide (DCC) followed by carrying out ester de-protection, and a method consisting of condensing orotic acid and an amino acid or amino acid ester using a mixed acid anhydride method (see, for example, Patent Document 5). The following documents (Patent Document 6, Non-Patent Document 1) may be referred to regarding other synthesis methods found in the literature.

<Agents>

The present invention provides a melanin production inhibitor in one embodiment thereof. This melanin production inhibitor contains as an active ingredient thereof an orotic acid derivative represented by the aforementioned general formula (1) or a salt thereof.

This melanin production inhibitor acts on cells that produce melanin and has an inhibitory effect on the production of melanin by these cells. The melanin production inhibitory effect can be confirmed by, for example, the method described in the examples. More specifically, in the case of comparing a cell population contacted with a melanin production inhibitor and a cell population not contacted with a melanin production inhibitor, and the cell population that has been contacted with the melanin production inhibitor produces a lower amount of melanin per cell, the melanin production inhibitor can be judged to have the effect of inhibiting production of melanin.

The present invention provides a whitening agent in one embodiment thereof. This whitening agent contains as an active ingredient thereof an orotic acid derivative represented by the aforementioned general formula (1) or a salt thereof.

Since the orotic acid derivative or salt thereof has a melanin production inhibitory effect, an agent containing the orotic acid derivative or salt thereof has a whitening effect, thereby making it possible to be provided as a whitening agent.

The present invention provides a fibroblast activator in one embodiment thereof. This fibroblast activator has as an active ingredient thereof an orotic acid derivative represented by the aforementioned general formula (1) or a salt thereof.

This fibroblast activator acts on fibroblasts and has an activating effect on fibroblasts. This fibroblast activating effect can be confirmed by, for example, the method described in the examples by using the amount of fiber production by fibroblasts as an indicator. In the case of comparing a cell population contacted with the fibroblast activator and a cell population not contacted with the fibroblast activator, and the cell population contacted with the fibroblast activator has a higher amount of fiber produced per cell, the fibroblast activator can be judged to have the effect of activating fibroblasts. Examples of fibers include collagen, elastin and hyaluronic acid.

The present invention provides a collagen and/or elastin production promoter in one embodiment thereof. This collagen and/or elastin production promoter contains as an active ingredient thereof an orotic acid derivative represented by the aforementioned general formula (1) or a salt thereof.

Since the orotic acid derivative or salt thereof has the effect of promoting production of collagen and/or elastin, an agent containing this orotic acid derivative or salt thereof can be provided as a collagen and/or elastin production promoter.

The present invention provides a wrinkle ameliorant in one embodiment thereof. This wrinkle ameliorant contains as an active ingredient thereof an orotic acid derivative represented by the aforementioned general formula (1) or a salt thereof.

Since the orotic acid derivative or salt thereof has an action of promoting production of collagen and/or elastin, an agent containing the orotic acid derivative or salt thereof can be provided as a wrinkle ameliorant that has the effect of improving wrinkles.

Each type of agent of the embodiments as described above is only required to contain one or more types of ingredients selected from the group consisting of Compound (1) and a salt thereof as essential ingredients. Thus, these agents may contain Compound (1) but not contain a salt of Compound (1), may contain a salt of Compound (1) but not contain Compound (1), or may contain both Compound (1) and a salt of Compound (1).

The Compound (1) contained in each type of agent of the embodiments as described above may consist of only one type or may consist of two or more types. In the case of consisting of two or more types, the combination and ratio thereof can be suitably selected according to the objective. Similarly, a salt of Compound (1) contained in the agents may consist of only one type or may consist of two or more types. In the case of consisting of two or more types, the combination and ratio thereof can be suitably selected according to the objective.

Each type of agent of the embodiments as described above may be administered orally or parenterally. For example, each type of agent can be provided orally in the form of, for example, a tablet, coated tablet, pill, powder, granule, liquid, suspension or emulsion, or in the form of an injection preparation, suppository or external skin preparation.

Each type of agent of the embodiments as described above may be provided as an external skin preparation.

This external skin preparation contains an orotic acid derivative represented by the aforementioned general formula (1) or a salt thereof. In addition, a cosmetic of the embodiments as described above contains an orotic acid derivative represented by the aforementioned general formula (1) or a salt thereof. The external skin preparation of the present embodiment can also be used as a cosmetic.

Examples of types of the aforementioned external skin preparations and cosmetics include hair cosmetics such as shampoo, oil shampoo, cream shampoo, conditioning shampoo, dandruff shampoo, hair coloring shampoo, rinse-containing shampoo, rinse, treatment, hair pack, hair foam, hair mousse, hair spray, hair mist, hair wax, hair gel, water-based grease, hair setting lotion, coloring lotion, hair tonic, hair liquid, pomade, hair cream stick, hair cream, hair blow, split end coating treatment, hair oil, permanent wave agent, hair straightening agent, oxidative hair dye, hair bleach, hair coloring pretreatment, hair coloring after-treatment, permanent pretreatment, permanent after-treatment, hair manicure or hair growth formula; foundation cosmetics such as facial wash, cleansing foam, cleansing powder, facial cleansing powder, cleansing cream, cleansing milk, cleansing lotion, cleansing gel, cleansing oil, cleansing mask, beauty wash, softening beauty wash, astringent beauty wash, cleansing beauty wash, multilayered beauty wash, milky liquid, emollient lotion, moisture lotion, milky lotion, nourishing lotion, nourishing milk, skin moisturizer, moisturizing emulsion, massage lotion, cleansing lotion, protective emulsion, sun protection, sun protector, UV care milk, sunscreen, makeup lotion, keratin smoother, elbow lotion, hand lotion, body lotion, cream, emollient cream, nutrient cream, nourishing cream, vanishing cream, moisturizing cream, night cream, massaging cream, cleansing cream, makeup cream, base cream, pre-makeup cream, sunscreen cream, suntan cream, depilatory cream, deodorant cream, shaving cream, keratin softening cream, gel, cleansing gel, moisturizing gel, soap, cosmetic soap, transparent soap, medicinal soap, liquid soap, shaving soap, synthetic cosmetic soap, pack, mask, peal-off pack, powder pack, washing pack, oil pack, cleansing mask, essence, moisturizing essence, whitening essence, UV protective essence, liposome beauty liquid or liposome beauty wash; makeup cosmetics such as face powder/dusting powder, foundations, makeup base, lipstick, lip gloss, rouge, eyeliner, mascara, eye shadow, eyebrow pencil, eyebrow highlighter, nail polish, nail polish remover or nail treatment; aromatic cosmetics such as cologne, perfume, parfum, eau de parfum, eau de toilette, eau de cologne, solid perfume, aromatic powder, scented soap, body lotion or bath oil; body cosmetics such as body shampoo, body cleanser, body powder, deodorant lotion, deodorant powder, deodorant spray, deodorant stick, deodorant cosmetics, decolorant, depilatory/hair removal agent, bath additive, insect repellent spray or insect repeller; ny and ointments, patches, lotions, liniments and liquid coating agents.

Examples of drug forms of the aforementioned external skin preparations and cosmetics include emulsion types such as oil-in-water (O/W) types, water-in-oil (W/O) types, W/O/W types or O/W/O types, emulsified polymer type; oily type; solid type; liquid type; paste type; stick type; volatile oil type; powders, jellies, gels, pastes, creams, sheets, films, mists, sprays, laminates, foams and flakes.

Examples of ingredients normally used in external skin preparations or cosmetics include raw materials described in existing raw material specifications or standards, and ingredients such as carriers or additives pharmaceutically allowed for use as external skin preparations.

Examples of raw materials described in existing specifications or standards include those described in the Japanese Pharmacopoeia, 14th Edition (Pharmaceutical and Medical Device Regulatory Science Society of Japan, ed., Jiho Inc., pub., April 2001), Japanese Standards of Cosmetic Ingredients, 2nd Edition, Analysis and Commentary, Pharmaceutical and Medical Device Regulatory Science Society of Japan, ed., Yakuji Nippo Ltd., pub., 1984), Japanese Cosmetic Ingredients Codex (compiled by the Ministry of Health and Welfare, Pharmaceutical Affairs Bureau, Examination Division, Yakuji Nippo Ltd., pub., 1993), Japanese Cosmetic Ingredients Codex Supplement (compiled by the Ministry of Health and Welfare, Pharmaceutical Affairs Bureau, Examination Division, Yakuji Nippo Ltd., pub., 1993), Cosmetic Comprehensive Licensing Standards (compiled by the Ministry of Health and Welfare, Pharmaceutical Affairs Bureau, Examination Division, Yakuji Nippo Ltd., pub., 1993), International Cosmetic Ingredient Dictionary and Handbook 2002, Ninth Edition, Vols. 1-4, compiled by CTFA, and the Cosmetics Raw Materials Dictionary (Nikko Chemicals Co., Ltd., pub., 1991).

The content or the aforementioned orotic acid derivative or salt thereof in each type of agent of the embodiments described above may be 0.05 µmol/L to 100 mmol/L, 0.5 µmiol/L to 10000 µmol/L or 20 µmol/L to 500 µmol/L. As a result of making the content to be within the aforementioned ranges, the aforementioned melanin production inhibitory effect, whitening effect, fibroblast activating effect, collagen and/or elastin production promoting effect and wrinkle improving effect are preferably demonstrated.

With respect to the melanin production inhibitory effect and whitening effect, the content of the aforementioned orotic acid derivative or salt thereof in the aforementioned agents may be 0.1 mmol/L to 100 mmol/L or 1 mmol/L to 70 mmol/L.

With respect to the fibroblast activating effect, collagen and/or elastin production promoting effect and wrinkle improving effect, the content of the aforementioned orotic acid derivative or salt thereof in the aforementioned agents may be 0.05 µmol/L to 1000 µmol/L or 0.5 µmol/L to 500 µmol/L.

The concentration of the aforementioned orotic acid derivative or salt thereof contained in each type of agent of the embodiments described above may be $1.0 \times 10^{-6}\%$ (w/v) to 10% (w/v), $1.0 \times 10^{-5}\%$ (w/v) to 5% (w/v), or $1.0 \times 10^{-4}\%$ (w/v) to 1% (w/v).

As a result of making the content to be within the aforementioned ranges, the aforementioned melanin production inhibitory effect, whitening effect, fibroblast activating effect, collagen and/or elastin production promoting effect and wrinkle improving effect are preferably demonstrated.

With respect to the melanin production inhibitory effect and whitening effect, the concentration of the aforementioned orotic acid derivative or salt thereof contained in the aforementioned agents may be $1.0 \times 10^{-2}\%$ (w/v) to 10% (w/v) or $5 \times 10^{-2}\%$ (w/v) to 5% (w/v).

With respect to the fibroblast activating effect, collagen and/or elastin production promoting effect and wrinkle improving effect, the concentration of the aforementioned orotic acid derivative or salt thereof in the aforementioned agents may be $1.0 \times 10^{-6}\%$ (w/v) to $1.0 \times 10^{-2}\%$ (w/v) or $1.0 \times 10^{-4}\%$ (w/v) to $5.0 \times 10^{-3}\%$ (w/v).

Each type of agent of the embodiments described above may also contain a polar solvent or contain a protic polar solvent. Examples of protic polar solvents include water and alcohols. Examples of alcohols include ethanol.

Each type of agent of the embodiments described above may also contain water and/or alcohol. In the case the agent contains water and/or alcohol, the content of water and/or alcohol based on 100% by weight of the agent may be 1% by weight to 99.9% by weight, 10% by weight to 90% by weight, 15% by weight to 60% by weight or 20% by weight to 40% by weight.

In the case the agent contains an alcohol, the content of alcohol based on 100% by weight of the agent may be 1% by weight to 40% by weight or 5% by weight to 30% by weight.

In the case the agent contains these polar solvents, if R of the orotic acid derivative represented by the aforementioned formula (1) is a side chain of a hydrophilic amino acid, solubility in these solvents is greater than that of orotic acid, thereby making this preferable.

In the case the agent contains water, the pH thereof may be 2 to 8, 4 to 7.5 or 6.5 to 7.5. In addition, if R of the orotic acid derivative represented by the aforementioned formula (1) at that time is a side chain of a hydrophilic amino acid, solubility in water is greater than that of orotic acid, thereby making this preferable. Furthermore, pH is the value determined at a temperature of 22° C.±2° C.

Although the dose of each type of agent of the embodiments described above cannot be uniformly defined since it varies according to such factors as the symptoms, body weight, or gender of the patient, the normal daily adult dose of the active ingredient (total dose of Compound (1) and salt thereof) is preferably 1 mg/person to 600 mg/person.

The prescribed amount of each agent is administered once per day or administered by dividing over several administrations per day.

In addition, although the amount used in the case agents of the embodiments described above are external skin preparations and cosmetics cannot be uniformly defined since it varies according to such factors as the symptoms, body weight, age or gender of the subject, the normal daily adult amount of active ingredient used (total amount of Compound (1) and salt thereof used) is preferably 1 mg/person to 600 mg/person.

The prescribed amount of the external skin preparation and cosmetic is used once per day or divided over several times per day.

The present invention provides a food additive in one embodiment thereof. The food additive contains Compound (1) of the aforementioned embodiments or a salt thereof. The food additive is only required to contain one or more types of ingredients selected from the group consisting of Compound (1) and a salt thereof as essential ingredients in the same manner as each type of agent of the embodiments described above such as external skin preparations and cosmetics. Thus, the food additive may contain Compound (1) but not contain a salt of Compound (1), may contain a salt of Compound (1) but not contain Compound (1), or may contain both Compound (1) and a salt of Compound (1).

Compound (1) contained in the food additive may consist of only one type or may consist of two or more types. In the case of consisting of two or more types, the combination and ratio thereof can be suitably selected according to the objective. Similarly, a salt of Compound (1) contained in the food additive may consist of only one type or may consist of two or more types. In the case of consisting of two or more types, the combination and ratio thereof can be suitably selected according to the objective.

The food additive may also contain optional ingredients known in the art in addition to Compound (1) or a salt thereof as necessary. There are no particular limitations on these optional ingredients and can be suitably selected according to the objective. One type of optional ingredient may be used alone or two or more types may be used in combination. In the case of using two or more types in combination, the combination and ratio thereof can be suitably selected according to the objective. There are no particular limitations on the content of optional ingredients in the food additive and may be suitably adjusted according to the objective.

There are no particular limitations on the total content of Compound (1) and a salt thereof (content of essential ingredient) in the aforementioned food additive, according to the objective, normally the total content is preferably 0.001% by weight to 0.5% by weight.

Although the amount of the food additive used cannot be uniformly defined since it varies according to the specific objective, the adult daily intake of active ingredient (total intake of Compound (1) and a salt thereof) is preferably 10 mg/person to 1000 mg/person.

The food additive can be in various forms such as a tablet, coated tablet, pill, powder, granule, capsule, liquid, suspension or emulsion in the same manner as known food additives.

Each type of agent of the embodiments described above can be produced by incorporating and formulating Compound (1) or a salt thereof along with other ingredients as necessary.

External skin preparations, cosmetics and food additives can be produced in the same manner as known external skin preparations, cosmetics and food additives with the exception of incorporating Compound (1) or a salt thereof.

In one embodiment thereof, the present invention provides a method for inhibiting melanin production comprising a step for administering an orotic acid derivative represented by the aforementioned general formula (1) or a salt thereof to a mammal or cultured cells thereof.

In one embodiment thereof, the present invention provides the use of an orotic acid derivative represented by the aforementioned general formula (1) or a salt thereof for producing a melanin production inhibitor, and an orotic acid derivative represented by the aforementioned general formula (1) or a salt thereof for inhibiting melanin production.

In one embodiment thereof, the present invention provides the use of an orotic acid derivative represented by the aforementioned general formula (1) or a salt thereof for producing a whitening agent, and an orotic acid derivative represented by the aforementioned general formula (1) or a salt thereof for skin whitening.

In one embodiment thereof, the present invention provides a method for activating fibroblasts comprising a step of administering an orotic acid derivative represented by the aforementioned general formula (1) or a salt thereof to a mammal or cultured cells thereof.

In one embodiment thereof, the present invention provides the use of an orotic acid derivative represented by the aforementioned general formula (1) or a salt thereof for producing a fibroblast activator, and an orotic acid derivative represented by the aforementioned general formula (1) or a salt thereof for activating fibroblasts.

In one embodiment thereof, the present invention provides a method of promoting the production of collagen and/or elastin comprising a step of administering an orotic acid derivative represented by the aforementioned general formula (1) or a salt thereof to a mammal or cultured cells thereof.

In one embodiment thereof, the present invention provides the use of an orotic acid derivative represented by the aforementioned general formula (1) or a salt thereof for producing a collagen and/or elastin production promoter, and an orotic acid derivative represented by the aforementioned general formula (1) or a salt thereof for promoting production of collagen and/or elastin.

In one embodiment thereof, the present invention provides a method of improving wrinkles comprising a step of administering an orotic acid derivative represented by the aforementioned general formula (1) or a salt thereof to a mammal or cultured cells thereof.

In one embodiment thereof, the present invention provides the use of an orotic acid derivative represented by the aforementioned general formula (1) or a salt thereof for producing a wrinkle ameliorant, and an orotic acid derivative represented by the aforementioned general formula (1) or a salt thereof for improving wrinkles.

Since the orotic acid derivative in each type of agent of the embodiments described above enables solubility in solvent to be controlled by converting orotic acid to an amino acid derivative, the orotic acid derivative can be made to demonstrate superior solubility in a desired solvent. In addition, a suitable solvent can be selected as necessary and the orotic acid derivative can be provided in various forms such as an aqueous preparation, emulsion, solid, powder or tablet.

Since the orotic acid derivative is a derivative of an amino acid, it can be expected to be highly safe. In addition, the orotic acid derivative demonstrates superior physiological activity as a result of having superior solubility in the case of being applied to a preparation, the body or cells and the like.

The melanin production inhibitor, whitening agent, fibroblast activator, collagen and/or elastin production promoter and wrinkle ameliorant of the aforementioned embodiments (these agents may be abbreviated as the aforementioned agents of the embodiments) may be provided as an orotic acid derivative represented by the aforementioned general formula (1) or salt thereof per se or may be provided as a composition mixed with a suitable additive.

Each type of agent of the embodiments described above may contain other ingredients in addition to Compound (1) or a salt thereof that are normally used as additives as necessary within a range that does not impair the effects of the present invention. These agents may contain an additive such that the total content (% by weight) of Compound (1) or a salt thereof and the additive does not exceed 100% by weight. For example, an additive may be contained at a ratio of 100 ppm by weight to 99.9% by weight based on the total weight of the aforementioned agent.

Examples of additives include the subsequently described oily base, moisturizer, touch improver, surfactant, polymer, thickener/gelling agent, solvent, propellant, antioxidant, reducing agent, oxidizing agent, preservative, antibacterial agent, chelating agent, pH adjuster, acid, base, powder, inorganic salt, ultraviolet absorber, whitening agent, vitamin or derivative thereof, antiphlogistic, anti-inflammatory agent, hair growth agent, circulation promoter, stimulant, hormone, anti-wrinkle agent, anti-aging agent, skin tightener, cooling agent, warming agent, wound healing promoter, irritation mitigator, analgesic, cell activator, plant/animal/microbial extract, antipruritic, keratin exfoliant/keratolytic agent, antiperspirant, freshening agent, astringent, enzyme, nucleic acid, fragrance, coloring matter, colorant, dye, pigment, water, metal-containing compound, unsaturated monomer, polyvalent alcohol, polymer additive, anti-inflammatory analgesic, antifungal agent, antihistamine, hypnotic sedative, tranquilizer, antihypertensive agent, antihypertensive diuretic agent, antibiotic, anesthetic, antimicrobial substance, antiepileptic agent, coronary vasodilator, herbal medicine, auxiliary agent, wetting agent, astringent, thickener, tackifier, antipruritic drug, keratin softening exfoliant, oily raw material, ultraviolet blocker, disinfectant, antioxidative substance, liquid matrix, liposoluble substance, polymeric carboxylate, additive and metal soap. One type of these additives may be contained alone or two or more types may be contained in combination. Examples of these additives are described in, for example, Japanese Unexamined Patent Application, First Publication No. 2014-114291.

EXAMPLES

Although the following provides a more detailed explanation of the present invention by indicating examples thereof, the present invention is not limited in any way by these examples. M represents mol/L unless specifically indicated otherwise. (w/v) represents (weight/volume).

Example 1

Study of Effect of pH on Water Solubility of Orotic Acid and Orotic Acid Derivatives The following compounds were prepared as orotic acid derivatives.

Compound represented by the aforementioned formula (1-2) (indicated as "Orotic acid-Gly" or "Orotic acid-Glycine")

Compound represented by the aforementioned formula (1-1) (indicated as "Orotic acid-Glu" or "Orotic acid-glutamic acid")

Compound represented by the aforementioned formula (1-4) (indicated as "Orotic acid-Asp" or "Orotic acid-aspartic acid")

Compound represented by the aforementioned formula (1-3) (indicated as "Orotic acid-His" or "Orotic acid-Histidine")

Orotic acid or each sample of the aforementioned orotic acid derivatives were weighed out in a 10 mL sample bottle and after adding pure water and stirring for 15 hours at room temperature (22° C.±2° C.), the sample was confirmed to be left undissolved followed by collection of 1 mL of supernatant. Subsequently, the pH of the remaining sample solution was adjusted using 1.0 N or 0.05 N aqueous sodium hydroxide solution, and in the case all of the sample had dissolved in the solution, sample was further added followed by stirring for 15 hours at room temperature (22° C.±2° C.) so that some of the sample was left undissolved and 1 mL of supernatant was similarly collected. Supernatant was repeatedly collected while adjusting the pH as necessary to obtain samples.

At this time, the pH was adjusted over a range of 2.3 to 7.2, which is generally used for external skin preparations and cosmetics. The resulting samples were filtered with a membrane filter having a pore size of 22 μm followed by subjecting the resulting filtrate to high-performance liquid chromatography (HPLC).

HPLC analyses were carried out using the LC Solution and PDA detector (CBM-20A) manufactured by Shimadzu Corp. and the Shodex RSpak DM-614 column at a column temperature of 40° C. and flow rate of 0.8 ml/min while using 0.02% $H_3PO_4$ for the mobile phase.

The concentration of each sample dissolved in solution was calculated from the area of the peak that coincided with each sample in the resulting analysis data. The results are shown in Table 1 and FIG. 1.

TABLE 1

| | | | | | | | | |
|---|---|---|---|---|---|---|---|---|
| Orotic acid | Saturated concentration (%) | 0.08 | | | 0.27 | 0.26 | 0.19 | 0.16 |
| | pH | 2.3 | | | 4.6 | 4.8 | 5.8 | 7.1 |
| Orotic acid-Gly | Saturated concentration (%) | 0.11 | 0.32 | | 0.55 | 1.66 | 3.83 | 6.60 |
| | pH | 2.8 | 3.6 | | 4 | 4.5 | 5.1 | 6.1 |
| Orotic acid-Glu | Saturated concentration (%) | 1.30 | | | | | | 5.43 |
| | pH | 2.3 | | | | | | 5.2 |
| Orotic acid-Asp | Saturated concentration (%) | 0.95 | 9.82 | >11.1 | | | | |
| | pH | 2.3 | 4.0 | 4.2 | | | | |
| Orotic acid-His | Saturated concentration (%) | | | | | | 0.22 | 1.25 |
| | pH | | | | | | | 4.9 | 7.2 |

In the table, % represents % (w/v).

Results

Remarkable improvement of solubility was observed over the test pH range for the orotic acid derivatives in comparison with orotic acid.

Example 2

Measurement of Cell Survival Rate in Human Three-Dimensional Skin Equivalent The effect of inhibiting melanin production in human three-dimensional skin was examined. Human three-dimensional skin equivalent manufactured by MatTek Corp. was purchased and pre-cultured for 1 hour with the dedicated culture medium, EPI-100LLMM, available from the same manufacturer.

Following pre-culturing, orotic acid-glutamic acid dissolved in phosphate-buffered saline (PBS) was added to the skin surface at a final concentration of 0.2% (w/v), 0.5% (w/v) or 1.0% (w/v), or orotic acid was added to the skin surface at a final concentration of 0.5% (w/v), followed by culturing for 15 days. The cell survival rates of the human three-dimensional skin equivalent following addition of orotic acid or orotic acid-glutamic acid were measured using the Cell Count Reagent SF manufactured by Nacalai-Tesque, Inc. After culturing, the skin was transferred to medium containing 1% Cell Count Reagent SF and after culturing for 3 hours, absorbance was measured at 750 nm. Cell survival rates were calculated as the measured value based on a value of 1 for the control.

The results are shown in Table 2. In the case of orotic acid-glutamic acid, there were no decreases in cell survival rates observed at the test concentrations, thereby confirming safety at the test concentrations.

TABLE 2

| | Cell Survival Rate (Relative Value) |
|---|---|
| Control (PBS) | 1 |
| 0.5% Orotic acid | 1.1 |
| 0.2% Orotic acid-glutamic acid | 1.4 |
| 0.5% Orotic acid-glutamic acid | 1.2 |
| 1% Orotic acid-glutamic acid | 0.9 |

In the table, % represents % (w/v).

Example 3

Effect of Inhibiting Melanin Production in Human Three-Dimensional Skin Equivalent After measuring cell survival rates in Experimental Example 2, the skin was thoroughly rinsed with PBS followed by sampling the skin and recovering in a 1.5 mL microtube. 150 μL of a dissolving solution containing sodium dodecyl sulfate (1% (w/v)), 0.05 mM ethylenediaminetetraacetate and 10 mM Tris-HCl (pH 6.8) were added thereto. After stirring, 3 μL of 5 mg/mL protease K were added followed by dissolving for 6 hours at 45° C., adding 25 μL of 500 mM $Na_3CO_3$ and 5 μL of 30% aqueous hydrogen peroxide and further treating for 30 minutes at 80° C. After allowing the sample to cool to room temperature, 20 μL of a 2:1 solution of chloroform and methanol were added to the sample followed by centrifuging for 10 minutes at the highest rotating speed of the centrifuge. 80 μL aliquots of the sample supernatant were recovered onto microplates followed by measurement of absorbance at 405 nm. Melanin production rate was determined by calculating the extinction coefficient of each sample based on a value of 1 for the control and dividing that value by the cell survival rate determined in Example 2 to calculate the melanin production rate per cell.

The results are shown in Table 3. Orotic acid and orotic acid derivatives were indicated to have a superior effect of inhibiting melanin production.

TABLE 3

| | Melanin Production Rate (relative value) |
|---|---|
| Control (PBS) | 1 |
| 0.5% Orotic acid | 0.70 |
| 0.2% Orotic acid-glutamic acid | 0.61 |
| 0.5% Orotic acid-glutamic acid | 0.71 |
| 1% Orotic acid-glutamic acid | 0.50 |

In the table, % represents % (w/v).

Example 4

Study of Collagen and Elastin Expression Promoting Effect in Fibroblasts

A study was made of the expression of collagen and elastin in aged human fibroblasts. Furthermore, expression levels of collagen and elastin are known to decrease and cause wrinkles as a result of cell aging.

Aged fibroblasts were prepared. Normal human fibroblasts in the form of NB1RGB cells (purchased from the Bioresource Center of Riken Japan) were cultured to confluence in a culture flask, and after culturing for 1 hour in Dulbecco's Modified Eagle Medium (DMEM) manufactured by Sigma Corp. containing 600 μM aqueous hydrogen peroxide and 10% (w/v) fetal calf serum, the cells were washed with PBS and cultured for 24 hours after changing the medium to DMEM containing 10% (w/v) fetal calf serum. This procedure was repeated three times to obtain aged fibroblasts.

The resulting aged fibroblasts were seeded into a plastic Petri dish at a seeding density of about 10,000 cells/$cm^2$ and then cultured for 24 hours in Dulbecco's Modified Eagle Medium (DMEM) manufactured by Sigma Corp. containing 10% (w/v) fetal calf serum. Subsequently, orotic acid or an orotic acid derivative dissolved in purified water (Table 4) was added to the medium at a final concentration of 100 µmol/l followed by additionally culturing for 24 hours. The medium to which orotic acid or orotic acid derivative had not been added was used as a control.

The culture supernatant was recovered after culturing and collagen production was measured using a human collagen type I ELISA kit manufactured by Acel, Inc. 50 µL of culture supernatant of each sample were added to a microplate treated with collagen antibody provided with the kit. After shake culturing for 1 hour at room temperature, the plate was washed three times with the washing solution provided with the kit. 50 µL of horseradish peroxidase-avidin reagent provided with the kit were added thereto followed by shake culturing for 1 hour at room temperature. After again washing three times with the washing solution, 50 µL of the coloring solution provided with the kit were added followed by allowing to stand undisturbed for 15 minutes at room temperature and adding 50 µL aliquots of reaction stopping solution thereto. After mixing by shaking for 1 minute, absorbance was measured at 450 nm.

The results are shown in Table 4. The orotic acid derivatives were determined to promote collagen production more efficiently than orotic acid.

TABLE 4

|  | Collagen Production (relative value) |
| --- | --- |
| Control | 1.00 |
| 100 µM (1.56 × 10⁻³%) Orotic acid | 1.14 |
| 100 µM (2.13 × 10⁻³%) Orotic acid-glycine | 1.23 |
| 100 µM (2.85 × 10⁻³%) Orotic acid-glutamic acid | 1.53 |
| 100 µM (2.93 × 10⁻³%) Orotic acid-histidine | 1.23 |

* In the table, % represent % (w/v).

Example 5

Confirmation of Elastin Production Promoting Effect

Elastin is a fibrous protein mainly having the function of connecting collagen molecules and is known to be present in the dermis of the skin and blood vessels as well as ligaments and impart tightness and elasticity to skin. The effect of orotic acid derivatives on the production of this elastin was verified using the method described below.

Normal human fibroblasts in the form of NB1RGB cells (purchased from the Bioresource Center of Riken Japan) were seeded at a seeding density of about 10,000 cells/cm² and cultured for 24 hours in DMEM medium containing 10% (w/v) fetal calf serum. An orotic acid derivative according to the present invention dissolved in pure water to a final concentration of 0 µM (control), 0.1 µM, 1 µM, 10 µM or 100 µM or orotic acid dissolved in purified water to a final concentration of 100 µM was added to DMEM medium containing 10% (w/v) fetal calf serum followed by culturing for 48 hours. The cells were subsequently recovered, the elastin was extracted with an elastin assay kit manufactured by Biocolor Ltd., and absorbance of the extract was measured at a wavelength of 513 nm.

The results are shown in Table 5. The orotic acid derivative was indicated to be more effective in promoting elastin production at a low concentration in comparison with orotic acid.

TABLE 5

|  | Elastin Production (relative value) |
| --- | --- |
| Control | 1.00 |
| 100 µM (1.86 × 10⁻³%) Orotic acid | 1.12 |
| 0.1 µM (2.85 × 10⁻⁶%) Orotic acid-glutamic acid | 1.20 |
| 1 µM (2.85 × 10⁻⁵%) Orotic acid-glutamic acid | 1.35 |
| 10 µM (2.85 × 10⁻⁴%) Orotic acid-glutamic acid | 1.24 |
| 100 µM (2.85 × 10⁻³%) Orotic acid-glutamic acid | 1.24 |

* In the table, % represents % (w/v).

Each of the configurations and combinations thereof in each embodiment are examples and configurations can be added, omitted, substituted and modified in other ways within a range that does not deviate from the gist of the present invention. In addition, the present invention is not limited to each of the embodiments, but rather is only limited by the scope of claim for patent (claims).

The invention claimed is:

1. A method for inhibiting melanin production, comprising applying a melanin production inhibitor to skin of a subject, said melanin production inhibitor comprising:
    an orotic acid derivative represented by the following general formula (1) or a salt thereof, as an active ingredient of the melanin production inhibitor:

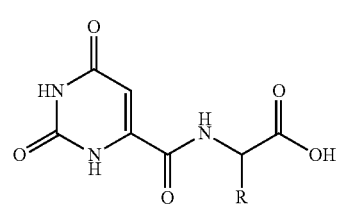

(1)

wherein, R represents a side chain of a naturally-occurring amino acid and R may form, together with a nitrogen atom adjacent thereto through a single carbon atom, a hetero ring.

2. A method for whitening the skin, comprising applying a whitening agent to skin of a subject, said whitening agent comprising:
    an orotic acid derivative represented by the following general formula (1) or a salt thereof, as an active ingredient of the whitening agent:

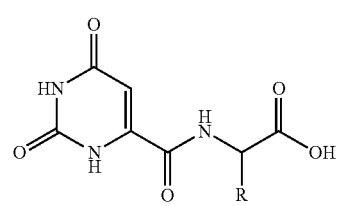

(1)

wherein, R represents a side chain of a naturally-occurring amino acid and R may form, together with a nitrogen atom adjacent thereto through a single carbon atom, a hetero ring.

3. A method for activating fibroblast, comprising applying a fibroblast activator to skin of a subject, said fibroblast activator comprising:
    an orotic acid derivative represented by the following general formula (1) or a salt thereof, as an active ingredient of the fibroblast activator:

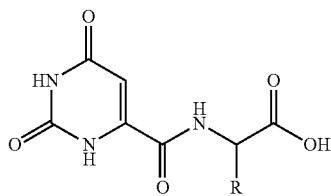

(1)

wherein, R represents a side chain of a naturally-occurring amino acid and R may form, together with a nitrogen atom adjacent thereto through a single carbon atom, a hetero ring.

4. A method for promoting collagen and/or elastin production, comprising applying a collagen and/or elastin production promotor to skin of a subject, said collagen and/or elastin production promotor comprising:

an orotic acid derivative represented by the following general formula (1) or a salt thereof, as an active ingredient of the collagen and/or elastin production promotor:

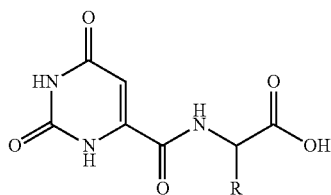

(1)

wherein, R represents a side chain of a naturally-occurring amino acid and R may form, together with a nitrogen atom adjacent thereto through a single carbon atom, a hetero ring.

5. A method for method for ameliorating wrinkles, comprising applying a wrinkle ameliorant to skin of a subject, said wrinkle ameliorant comprising:

an orotic acid derivative represented by the following general formula (1) or a salt thereof, as an active ingredient of the wrinkle ameliorant:

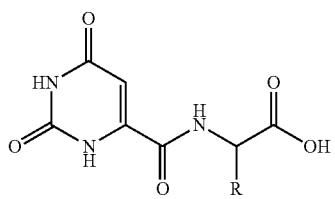

(1)

wherein, R represents a side chain of a naturally-occurring amino acid and R may form, together with a nitrogen atom adjacent thereto through a single carbon atom, a hetero ring.

6. The method according to claim 1, wherein the orotic acid derivative is represented by the following general formula (1-3) or (1-4):

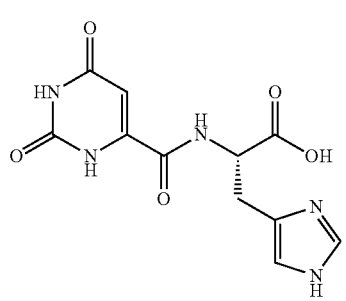

(1-3)

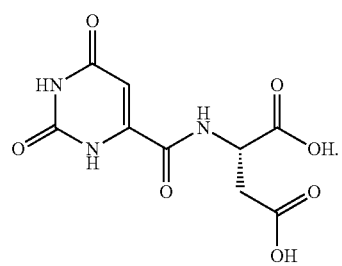

(1-4)

7. The method according to claim 2, wherein the orotic acid derivative is represented by the following general formula (1-3) or (1-4):

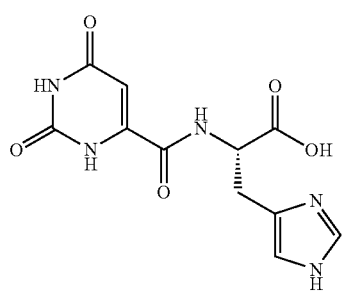

(1-3)

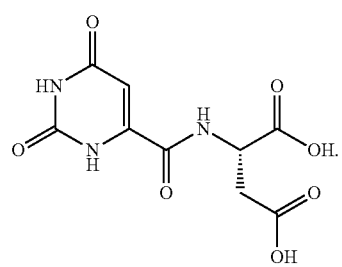

(1-4)

8. The method according to claim 3, wherein the orotic acid derivative is represented by the following general formula (1-3) or (1-4):

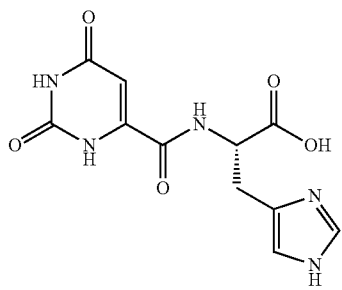
(1-3)

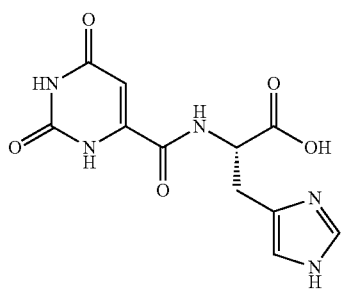
(1-3)

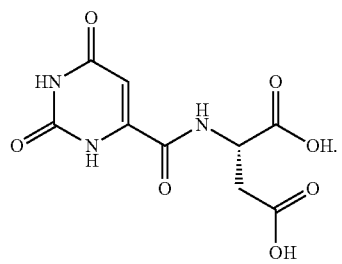
(1-4)

9. The method according to claim 4, wherein the orotic acid derivative is represented by the following general formula (1-3) or (1-4):

10. The method according to claim 5, wherein the orotic acid derivative is represented by the following general formula (1-3) or (1-4):

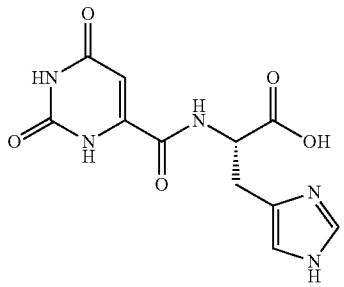
(1-3)

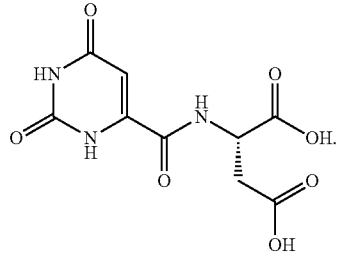
(1-4)

11. The method according to claim 1, wherein the melanin production inhibitor contains water, the water content is 10% by weight to 90% by weight, and the pH of the melanin production inhibitor is 4 to 7.5.

12. The method according to claim 2, wherein the whitening agent contains water, the water content is 10% by weight to 90% by weight, and the pH of the whitening agent is 4 to 7.5.

13. The method according to claim 3, wherein the fibroblast activator contains water, the water content is 10% by weight to 90% by weight, and the pH of the fibroblast activator is 4 to 7.5.

14. The method according to claim 4, wherein the collagen and/or elastin production promoter contains water, the water content is 10% by weight to 90% by weight, and the pH of the collagen and/or elastin production promoter is 4 to 7.5.

15. The method according to claim 5, wherein the wrinkle ameliorant contains water, the water content is 10% by weight to 90% by weight, and the pH of the wrinkle ameliorant is 4 to 7.5.

* * * * *